United States Patent
Lehmann et al.

(10) Patent No.: US 12,064,273 B2
(45) Date of Patent: *Aug. 20, 2024

(54) CONE-BEAM COMPUTED TOMOGRAPHY WITH CONTINUOUS KV BEAM ACQUISITION

(71) Applicant: Siemens Healthineers International AG, Steinhausen (CH)

(72) Inventors: Mathias Lehmann, Zurich (CH); Reto Ansorge, Zurich (CH); Manuel Waser, Zurich (CH); Daniel Morf, Buch am Irchel (CH)

(73) Assignee: Siemens Healthineers International AG, Steinhausen (CH)

( * ) Notice: Subject to any disclaimer, the term of this patent is extended or adjusted under 35 U.S.C. 154(b) by 286 days.

This patent is subject to a terminal disclaimer.

(21) Appl. No.: 17/587,652

(22) Filed: Jan. 28, 2022

(65) Prior Publication Data
US 2022/0151572 A1    May 19, 2022

Related U.S. Application Data

(63) Continuation of application No. 16/835,648, filed on Mar. 31, 2020, now Pat. No. 11,298,088.

(51) Int. Cl.
*A61B 6/03* (2006.01)
*A61B 6/40* (2024.01)
(Continued)

(52) U.S. Cl.
CPC ............ *A61B 6/032* (2013.01); *A61B 6/4085* (2013.01); *A61B 6/4266* (2013.01); *A61B 6/583* (2013.01);
(Continued)

(58) Field of Classification Search
CPC ..... A61B 6/4266; A61B 6/4085; A61B 6/032; A61B 6/42; A61B 6/5205; A61B 6/4233;
(Continued)

(56) References Cited

U.S. PATENT DOCUMENTS

2004/0000630 A1    1/2004 Spartiotis
2005/0175139 A1    8/2005 Horiuchi et al.
(Continued)

FOREIGN PATENT DOCUMENTS

WO    2019014251 A    1/2019

OTHER PUBLICATIONS

A Nemtoi et al., "Cone beam CT: a current overview of devices," Dentomaxillofac Radiol v.42(8); Aug. 2013; 42(8), 11 pages [online], [retrieved on May 4, 2020]. Retrieved from the Internet <https://www.ncbi.nlm.nih.gov/pmc/articles/PMC3922261>.
(Continued)

*Primary Examiner* — Irakli Kiknadze
(74) *Attorney, Agent, or Firm* — Duane Morris LLP (57) ABSTRACT

A cone-beam computed tomography (CBCT) method uses a continuous beam and an area detector to carry out fast acquisition of projection data. The acquired projection data are then reconstructed to generate tomographic images. In acquisition of the projection data, a radiation source continuously irradiates a subject with a cone beam of radiation from a plurality of angles and an area detector continuously reads out data. A CBCT system including a source operable to produce a cone beam of radiation and an area detector movable in synchrony with the source to rapidly acquire projection data for CBCT construction is also disclosed.

19 Claims, 5 Drawing Sheets

(51) Int. Cl.
    *A61B 6/42*    (2024.01)
    *A61B 6/58*    (2024.01)
    *A61N 5/10*    (2006.01)
    *G06T 11/00*   (2006.01)
(52) U.S. Cl.
    CPC .......... *A61N 5/1077* (2013.01); *G06T 11/005* (2013.01); *G06T 11/006* (2013.01); *G06T 2211/424* (2013.01)
(58) Field of Classification Search
    CPC ........... A61B 6/583; A61B 6/40; A61B 6/482; A61B 6/469; A61B 6/4241; A61B 6/4007; A61B 6/035; A61B 6/0407; A61B 90/10; A61B 6/5288; A61B 6/5258; A61B 6/027; A61B 6/03; A61B 6/12; A61B 6/4014; A61B 6/4035; A61B 6/4441; A61B 6/5235; A61B 6/5282; A61B 6/542; A61B 6/585; A61B 6/06; A61B 2090/101; A61B 6/4078; A61B 6/5264; G06T 11/005; G06T 11/006; G06T 2211/424; G06T 7/0012; G06T 1/00; G06T 2207/10081; G06T 2211/421; G06T 2211/436; G06T 2211/412; G01N 23/046; G01N 2223/401; A61N 5/1077; A61N 2005/1061; A61N 5/1049; A61N 5/1045; A61N 5/103; A61N 5/1081; A61N 2005/1054; G01T 1/16

USPC ................................. 378/4, 19, 62
    See application file for complete search history.

(56) References Cited

U.S. PATENT DOCUMENTS

| | | |
|---|---|---|
| 2008/0002806 A1 | 1/2008 | Nishide et al. |
| 2010/0128839 A1 | 5/2010 | Partain et al. |
| 2012/0008740 A1 | 1/2012 | Dennerlein et al. |
| 2015/0356756 A1 | 12/2015 | Okamoto et al. |
| 2016/0278719 A1 | 9/2016 | Jensen et al. |
| 2017/0303868 A1 | 10/2017 | Lee |
| 2020/0155103 A1 | 5/2020 | Mistretta et al. |

OTHER PUBLICATIONS

R. Pauwels, "History of Dental Radiography: Evolution of 2D and 3D Imaging Modalities," Medical Physics International, vol. 8, No. 1, Mar. 2020, pp. 235-277.

J Morita MFG Corp., "3D Accuitomo 170," Technical Brochure, 26 pages, [online], [retrieved on May 18, 2020]. Retrieved from the Internet <https://www.morita.com/cms/files/Brochure_3D_Accuitomo_170-1.pdf?download=1>.

PCT, International Search Report and Written Opinion of the International Searching Authority in PCT/EP2021/057965 dated Jun. 14, 2021, 11 pages.

CONE-BEAM COMPUTED TOMOGRAPHY WITH CONTINUOUS KV BEAM ACQUISITION

CROSS-REFERENCE TO RELATED APPLICATIONS

The present application is a continuation of U.S. application Ser. No. 16/835,648 filed on Mar. 31, 2020, now U.S. Pat. No. 11,298,088 issued Apr. 12, 2022, which is incorporated herein by reference in its entirety for all purposes.

TECHNICAL FIELD

This disclosure in general relates to radiation imaging and treatment. In particular, various embodiments of cone-beam computed tomography (CBCT) with continuous kilovoltage (kV) beam acquisition are described.

BACKGROUND

Computed tomography (CT) is known in medical imaging and radiation therapy and has proved an invaluable tool for many clinical applications. In performing computed tomography, a radiation source emits x-rays into a portion of a subject from a plurality of angles, and a detector detects the radiation transmitted through the portion of the subject to acquire projection data. The projection data acquired are reconstructed using a reconstruction algorithm to generate a tomographic image in either a two-dimensional image slice or a three-dimensional image volume of the portion of the subject.

Conventional CBCT uses pulsed beams in acquisition of projection data. A radiation source emits beam pulses at a predetermined frequency and a detector detects signals generated by the beam pulses transmitted through the imaging portion. The emission of a pulse and detection of the pulse transmitted are operated sequentially. During detection of the pulse transmitted, no pulse is delivered to the body portion.

Conventional CBCT with pulsed beam acquisition significantly limits the duty cycle of a radiation source, the portion of operation of the radiation source during which radiation is produced. For example, in a kV-CBCT with pulsed beam operation, the duty cycle of a kV source can be limited to 30-40 percent. For large duty cycles, pulsed beam CT reduces the maximally possible frame rate of the detector due to the sequential operation of emission of a beam pulse and detection of the transmitted beam in acquisition of projection data. Furthermore, pulsed beams may cause measurement inaccuracy because a beam output practically cannot immediately stop at the end of a pulse, but may take several milliseconds until the intensity falls to zero. This so-called tail effect may create imaging artifacts, which can be relatively large when short pulses are used.

Therefore, there is a continuing need for improved computed tomography to mitigate the problems of conventional CBCT. It would be desirable to provide a CBCT method and system that allows for a radiation source to operate at a 100 percent duty cycle. It would be desirable to provide a CBCT method and system using a continuous beam to rapidly acquire projection data and generate reconstructed images with improved image quality.

SUMMARY OF THE DISCLOSURE

A CBCT method with continuous kV beam acquisition is disclosed. The method comprises acquiring a plurality of projections of at least a portion of a subject using a radiation source and an area detector, wherein in acquiring the plurality of projections of data set, the source continuously irradiates the portion of the subject with a cone beam of radiation from a plurality of angles and the area detector reads out data during the continuous irradiating of the portion of the subject with the cone beam of radiation. A tomographic image of the portion of the subject is constructed based on at least a portion of the plurality of projections of data set.

A CBCT system is disclosed. The system comprises a radiation source, an area detector movable in synchrony with the radiation source, and an image processing device. The radiation source is operable to produce a cone beam of radiation and movable relative to a subject to irradiate at least a portion of the subject from a plurality of angles. The area detector being operable to acquire a plurality of projections of the portion of the subject while the source continuously irradiates the portion of the subject with the cone beam of radiation from the plurality of angles. The image processing device is configured to reconstruct a tomographic image of the portion of the subject based on at least a portion of the plurality of projections of data set.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages of the disclosure will become better understood upon reading of the following detailed description and the appended claims in conjunction with the accompanying drawings, where:

DETAILED DESCRIPTION OF EMBODIMENTS

With reference to FIGS. 1-5, various embodiments of a CBCT method and system will now be described. In general, an example CBCT method uses a continuous cone beam of radiation and an area detector to carry out fast acquisition of projection data. The acquired projection data are then reconstructed to generate tomographic images, with image quality better than or at least comparable to that of conventional CBCT with pulsed beams. Before reconstruction of tomographic images, the acquired projection data are optionally pre-processed to correct or compensate possible geometrical error arising from acquisition with a continuous beam and area detector.

Acquisition of projection data with a continuous beam and an area detector effectively increases the duty cycle of a radiation source, up from the currently common 30 to 40 percent duty cycle to 100 percent duty cycle according to embodiments of the disclosure. As such, an increased kV imaging dose can be delivered during a limited time span. In conventional kV-CBCT acquisition on radiation therapy (RT) machines, a pulsed-beam operation represents a kV-source duty cycle typically of 30% to maximal 40%, for instance in an acquisition where a kV pulse length is 20 milliseconds (ms) and an imager operates at 15 frames per second (fps), or in an acquisition where a kV pulse length is 10 ms and an imager operates at 30 fps. For a given source power, the pulsed operation limits the total amount of dose or mAs exposure that can be delivered during a given time period. Milliampere-seconds, or mAs, is a measure of radiation produced (milliamperage) over a set amount of time (seconds) via an x-ray tube. With a continuous kV beam operation according to the disclosure, a 100% source duty cycle allows delivering about 2.5 times more dose in the same time.

As an example, in a conventional kV-CBCT scan (e.g. Pelvis scan) for acquisition of 900 projections with a total dose of 1080 mAs, using an x-ray tube operating at 125 kV, 20 ms beam pulse length, 60 mA pulse current, and an imager operating at 15 fps, a total 18-second beam time requires a long 60-second scan time. According to embodiments of the disclosure, with a continuous beam at the same current (60 mA), the same amount of dose (1080 mAs) can be delivered in 18 seconds.

As another example, radiation treatment (RT) machines have been developed allowing a gantry to rotate 360° in less than 17 seconds for treatment delivery. However, for a CBCT on such RT machines, a current CBCT scan mode with the highest dose (e.g. Pelvis Large) takes a much longer time (41 seconds) to be delivered, mainly due to the limited duty cycle of the CBCT source (40 to 50 percent).

Acquisition of projection data with a continuous beam also increases the effective detection speed of the area detector such as a flat-panel imager. For a given readout time of a flat-panel imager, the maximal frame rate can be increased. In contrast to the conventional pulsed-beam operation where the emission of a kV-beam pulse and the readout of an imager frame are conducted sequentially, with a continuous beam operation according to the disclosure, the readout of an imager frame can be started practically immediately after the end of the readout of the previous frame. By way of example, in a pulsed beam operation with 20 ms kV-beam pulse and 20 ms imager readout time (40 ms cycle time), the imager operates at a frame rate of 25 fps. With a continuous beam operation according to the disclosure, the imager with the same readout time (20 ms) allows a frame rate of 50 fps (20 ms cycle time).

Acquisition of projection data with a continuous beam and an area detector can increase the lifetime of the radiation source such as an x-ray tube (filament). For example, a kV-tube lifetime is increased because a given dose can be delivered at a lower continuous current rather than in short pulses with high peak currents.

Acquisition of projection data with a continuous beam avoids kV pulse tail effects. In conventional pulsed-beam operation, a beam output does not immediately stop at the end of a pulse, but instead can take several milliseconds until the beam intensity falls to zero. This so-called tail can affect measurement accuracy. For short pulses, the contribution of the tail to the total signal or patient dose can become relatively large. Acquisition with a continuous beam according to the disclosure greatly reduces pulse-tail related effects.

Acquisition of projection data with a continuous beam also reduces aliasing artifacts in CBCT reconstruction. For objects moving across the image as the gantry rotates, an exposure with a 100 percent duty cycle leads to more blurred structures. In CBCT reconstructions, this lowers the spatial resolution far away from the rotation axis to some extent, but helps reducing aliasing (sampling) artifacts which may otherwise become clearly visible in cases with very short pulses.

Figure 1:
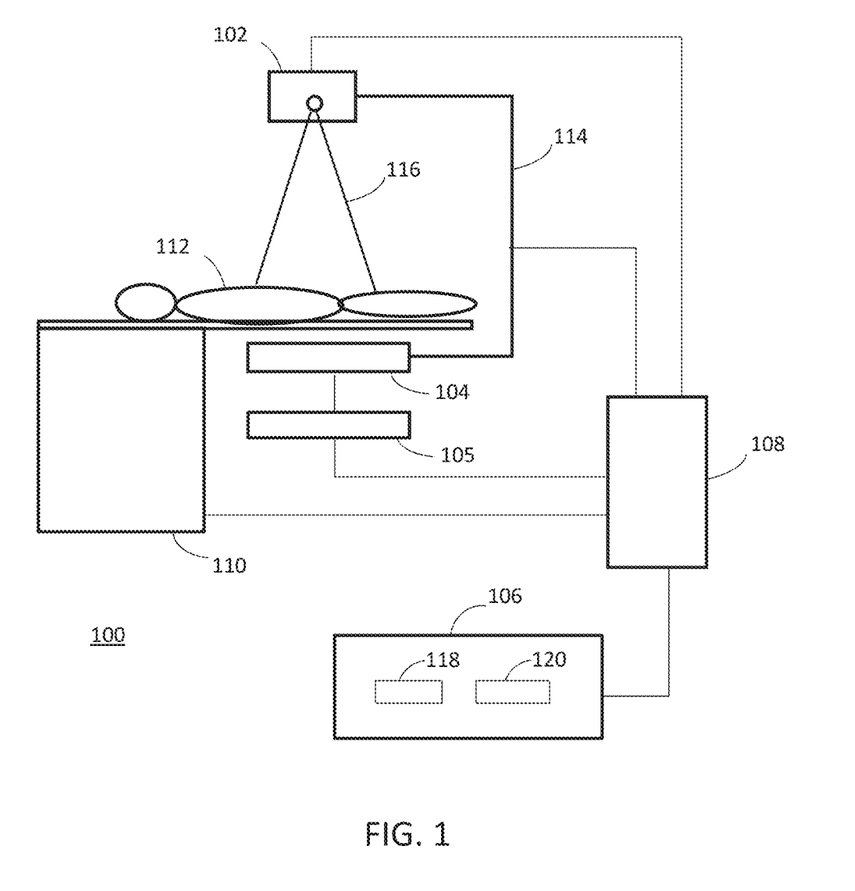
FIG. 1 depicts an example radiation system according to embodiments of the disclosure.

FIG. 1 depicts an example imaging or radiation system 100 in which embodiments of a method of the disclosure can be implemented. It should be noted that while embodiments of the disclosure are described in connection with an imaging system, the principle of the disclosure can be implemented in a treatment system, a simulation system, a research and developmental system or any other suitable radiation system including an imaging functionality. For example, embodiments of the disclosure may be embodied in a radiation treatment system which incorporates an imaging system shown in FIG. 1 and further includes a source operable at a megavoltage (MV) level e.g. 4 to 20 MV to produce radiation suitable for treatment.

As shown in FIG. 1, an example radiation system 100 in general includes a radiation source 102, an area detector 104, and an image processing device 106. The operation of the radiation source 102, area detector 104, and the image processing device 106 can be controlled by a computer and control system 108. A supporting device 110 e.g. a couch can place a subject 112 e.g. a patient between the source 102 and the area detector 104 to receive radiation for imaging and/or treatment.

The source 102 and the area detector 104 can be arranged opposite to each other and carried by a movable or rotatable gantry 114. As such, the source 102 and the area detector 104 can be moved in synchrony during acquisition of projections of the subject from multiple angles. The gantry 114 can be a ring gantry or a C-arm gantry operable to rotate the source 102 and the area detector 104 in an arc as known in the art. Alternatively, or additionally, the couch 110 supporting the subject 112 can be moved in multiple degrees of freedom, e.g. translated horizontally and/or vertically, and/or rotated about various axes, to position the subject 112 relative to the source 102 before or during acquisition of projection data.

In a specific embodiment, the source 102 is operable to produce a cone beam of radiation 116 and continuously irradiate the subject 112 from multiple angles by rotating the gantry 114. During irradiation with the continuous cone beam 116, the area detector 104 e.g. a flat-panel imager is operable to continuously readout data, allowing fast acquisition of multiple projections needed for CBCT reconstruction. In general, the number of projections needed for CBCT reconstruction ranges from 400 to 900, depending on the image quality acceptable for specific applications. However, the claims of the disclosure are not so limited. More than 900 or less than 400 projections can be acquired for CBCT reconstruction.

In a specific embodiment, the gantry 114 can rotate the source 102 and the area detector 104 at a relatively fast speed, e.g. at two 360°-rotations per minute or more, or at four 360°-rotations per minute or more. During a relatively high-speed rotation, the cone beam 116 from the source 102 remains on, continuously irradiating the subject 112 from a plurality of angles, and the area detector 104 continuously reads out data, thereby allowing the source 102 to operate at a 100 percent duty cycle. In a specific embodiment, multiple projections of at least a portion of the subject 112 are acquired during a single 360°-rotation of the source 102, during which the source 102 continuously emits a cone beam and the area detector 104 continuously readout data. In an alternative embodiment, a 360°-rotation is split in multiple sectors or pieces, for example, in 5 sectors each being a 72°-arc. In each of the multiple sectors or pieces, multiple projections are acquired during which the source 102 continuously emits a cone beam and the area detector 104 continuously readout data, allowing the source 102 to operate at a 100 percent duty cycle. The projection data acquired in the multiple sectors or pieces can be then combined, forming a full-360° data set.

In a specific embodiment, the source 102 is an x-ray tube operable at a kilovoltage (kV) level e.g. ranging from 50 to 150 kV with a peak kilovoltage (kVp) at e.g. 125 kVp. In a specific embodiment, the area detector is a flat-panel imager having a large active detection area, e.g. 20×20 $cm^2$ or greater, 30×30 $cm^2$ or greater, or 40×40 $cm^2$ or greater, or any size between 20×20 and 45×45 $cm^2$. The cone-beam 116 produced by the source 102 has a cone-beam angle. The cone-beam angle can be defined in a direction of the pixel column and/or row of a flat-panel imager. By way of example, for a flat-panel imager having an active detection area of 20×45 $cm^2$ centered on a cone beam, the cone-beam angle may range from 7 to 17 degrees, in the directions of both the pixel column and row of the imager. Other cone-beam angles can be adopted in conjunction with area detectors of different sizes. In alternative embodiments of the disclosure, the area detector may be arranged laterally offset with respect to the central line of the cone beam.

The rotation of the source 102 and the area detector 104 in synchrony around the subject 112 provides a reconstruction volume encompassing at least a portion of the subject 112 e.g. the pelvic region of a patient. A reconstruction volume is a volumetric space, generally in a cylindrical shape, over which a three-dimensional image can be reconstructed by the CBCT. The diameter of a reconstruction volume is typically referred to as the field of view (FOV). The length of a reconstruction volume is herein referred to as the scan length. The dimension of the FOV and scan length of a reconstruction volume may depend on the distance between the focal spot of the source 102 and the detection surface of the area detector 104, the cone angle of the beam 116 produced by the source 102, and the size of the detection surface of the area detector 104. In a specific embodiment, the distance between the focal spot of the source 102 and the detection surface of the area detector 104, the cone angle of the beam produced by the source 102, and the size of the detection surface of the area detector 104 can be selected such that the reconstruction volume has a FOV ranging from 25 to 50 centimeter or greater, and/or a scan length ranging from 15 to 28 centimeter or greater. It should be pointed out that the dimensions of the reconstruction volume are provided for illustrative purpose. As described above, the area detector can be arranged laterally offset with respect to the beam e.g. in a half-fan configuration, and the FOV and the scan length of the reconstruction volume can be more or less than the above example values.

The image processing device 106 may include a computer 118 and software 120 designed to reconstruct tomographic images based on the projections acquired. Various reconstruction software or algorithms are known in the art and can be used in conjunction with embodiments of the disclosure. For example, standard CBCT reconstruction software based on filtered back projection techniques can be used to generate tomographic images. Iterative CBCT reconstruction software based on algebraic reconstruction techniques, which becomes commercially available due to increasing computing power of computers, can also be used to generate tomographic images. In a specific embodiment, the software 120 implemented in the image processing device 106 can reconstruct projection data into tomographic images representing a three-dimensional volume of a portion of the subject.

In a specific embodiment, prior to reconstruction, the acquired projection data are pre-processed to account for radiation beam and detector properties and system electronic properties. For example, the acquired projection data can be pre-processed to correct detector pixel defects, account for electronic gain, or to apply logarithmic transformation etc. In a specific embodiment according to the disclosure, the projection data can be pre-processed to correct or compensate a geometric error or twist arising from acquisition with a continuous cone beam and an area detector, as will be described in greater detail below.

CBCT reconstruction algorithms generates 3D volumes based on a series of projections (frames) acquired while the gantry rotates. For many of the processing steps, the currently deployed algorithms assume that the pixel data in a single frame all represent the same time. For instance, the back projection of the pixel data assumes the same gantry position for all image rows in a given projection. If not taken into account, the systematic time delay introduced by a continuous beam acquisition would generate geometrical errors, as pixel data in e.g. the upper rows represent the situation during a slightly different gantry position. Without correction, this would lead to a geometric error corresponding to a slightly twisted cylinder.

By way of example, a CBCT system on an RT platform may include a flat-panel imager having a size or active detector area of 43×43 $cm^2$, a frame readout time of 20 ms, and positioned with lateral offset (Half-Fan configuration), and provides a CBCT reconstruction volume with a diameter of 49 cm. If the gantry of the RT platform rotates at a speed of 4 rotations per minute (RPM) (24° per second), the readout time of the flat-panel imager would correspond to a time delay of 10 ms between the central detector row and the top or bottom detector row of the imager. At 4 RPM, a structure located 24 cm from the isocenter axis (i.e. close to the edge of the reconstruction volume with a diameter of 49 cm) would move about 1 mm during 10 ms, in the frame of reference of the rotating imaging system. This means that if the structure is located such that its image is projected to the top detector row, its measured position could be up to 1 mm away from the position that would be observed in a pulsed system.

Because of the cone-beam geometry, a given imager row contributes to voxels lying on different slices of the volume, except for the central row of the imager which contributes only to the central slice. For this reason, the "de-twisting" of the reconstructed volume cannot simply be compensated by rotating back each slice of the volume by a well-defined small angle, which would only represent an inaccurate compensation.

According to a specific embodiment of the disclosure, the pre-processing of the projection data comprises weighting data of a given projection acquired in a given time period with data of a projection acquired after the given projection, and/or, with data of a projection acquired before the given projection. The pre-processing method according to the disclosure allows using the same reconstruction algorithms and therefore simplifies the introduction of this acquisition mode in existing CBCT reconstruction frameworks.

Figure 2:
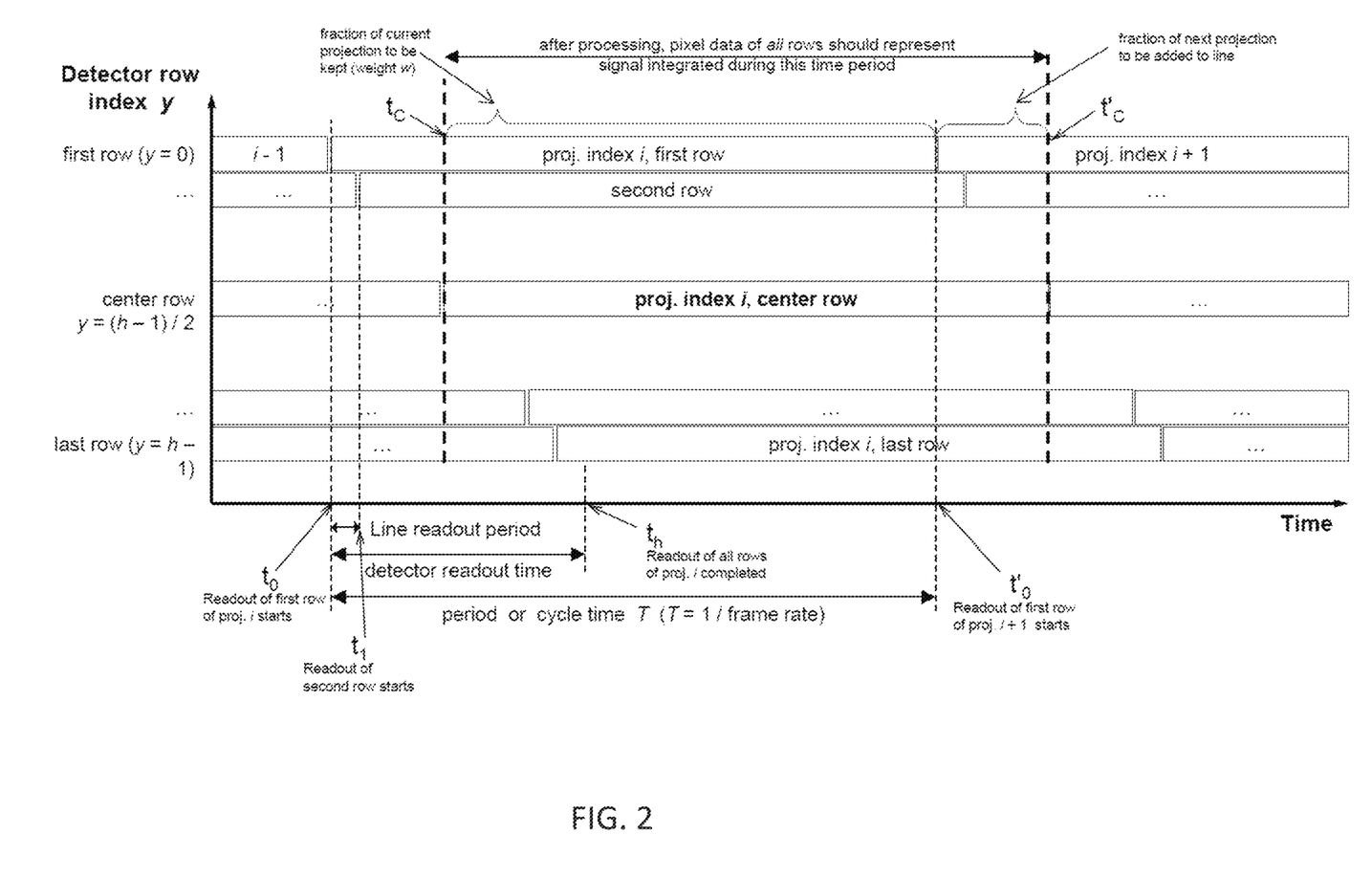
FIG. 2 is an example exposure time diagram illustrating a pre-processing method according to embodiments of the disclosure.

FIG. 2 is an example exposure time diagram illustrating the pre-processing method according to a specific embodiment of the disclosure. The area detector 104 used in acquisition of the projection data is a flat-panel imager comprising a plurality of detector pixels in columns and rows (the total number of rows is designated as h). In FIG. 2, the vertical axis represents the detector row; the horizontal axis represents time. For acquisition of a given projection (index i), the readout of the detector pixels starts from the first row (index y=0) at time t0, then the second row at t1 . . . the center row at tc, until finishing the last row at th. The time elapsing between the readout of successive rows, e.g. between the first and second rows, t1-t0, is herein referred to as line readout period (lineTime). The time that the imager takes to read out all of the rows is herein referred to as detector readout time. In the example as shown, the detector readout time can be given approximately by line-Time×number of rows.

After the readout of the given projection (index i), the readout of a next projection (index i+1) starts at time C0, continues to the center row at t'c, until finishing the last row of the projection. The time elapsing between the readout of successive projections or frames is herein referred to as period or cycle time (T). The cycle time can be determined by the detector frame rate (T=1/frame rate). For a continuous kV beam, it also represents the total time during which the kV beam signal is accumulated (integrated) in the pixel (exposure time). It is equal for all detector rows. The shortest cycle time (fastest frame rate) can be determined by the detector readout time, but a cycle time may also be considerably longer than detector readout time.

The timestamp associated with a given projection and the acquisition parameters such as the angular position of the gantry is defined relative to the central pixel row of the detector. One aim of pre-processing is to generate projection data where all pixel rows correspond to the same time (and gantry position), for example, defined arbitrarily by the central row of the detector. In the diagram shown in FIG. 2, for the given projection i, the first row is read out earlier than the central row. According to a specific embodiment of the disclosure, the pre-processing of projection i can use pixel data of the next projection (index i+1) for linear interpolation. The weight of the original data, w, can be determined by the relative time delay. Likewise, for the given projection i, the last row is read out later than the central row. Thus, the pre-processing of projection i can also use pixel data of the previous projection (index i−1) for the linear interpolation. The weight of the original data, w, can be determined by the relative time delay. By way of example, a weight can be given to the data value of a pixel of a given row (y) based on the time delay in reading out the data of the given row (y) relative to a reference row (y0) of the area detector.

In a specific embodiment, the weighting of pixel data of a given projection is carried out based on the linear interpolation as follows: replace pi( . . . ,y) by:

w*pi( . . . ,y)+(1−w)*pi+1( . . . ,y), where pi( . . . ,y) represents a data value of a pixel at row y of a given projection i acquired by the area detector comprising h rows of pixels and y<h/2, pi+1 ( . . . ,y) represents a data value of the pixel at row y of projection i+1, and w represents a weighting factor, and w=1−(h/2−y)*(lineTime/cycleTime), or replace pi( . . . ,y) by:

w*pi( . . . ,y)+(1−w)*pi−1( . . . ,y), where pi( . . . ,y) represents a data value of a pixel at row y of a given projection i acquired by the area detector comprising h rows of pixels and y>h/2, pi−1( . . . , y) represents a data value of the pixel at row y of projection i−1, and w represents a weighting factor, and w=1−(y−h/2)*(lineTime/cycleTime).

Embodiments of the disclosure will now be described in connection with working examples. It should be pointed out that while some specific details are set forth in the working examples in order to provide a thorough understanding of the disclosure, it will be apparent to one of ordinary skill in the art that some of these specific details may not be employed to practice embodiments of the disclosure. In other instances, some well-known details may not be described in order to avoid unnecessarily obscuring embodiments of the disclosure.

EXAMPLES

CBCT with a continuous kV beam and CBCT with a pulsed kV beam were evaluated on a HALCYON® radiation treatment (RT) machine equipped with a CBCT system, available from Varian Medical Systems, Inc. in Palo Alto, California. The CBCT system included an x-ray tube operated at 125 kVp and a flat-panel imager having 1280×1280 pixels and an active detector area of 43×43 cm². The flat-panel imager was read out at a binning mode (1×4) or pixel resolution of 1280×320. Phantoms used in the evaluation, Catphan® 504 and Body Phantom, were obtained from Phantom Laboratory in Salem, N.Y. Scans were performed in both clockwise and counter-clockwise directions for geometric accuracy tests. For CBCT with continuous kV beam acquisition, the x-ray tube was operated at 100 percent duty cycle. For CBCT with pulsed kV beam acquisition, the x-ray tube was operated at about 30 percent of duty cycle or lower. Some other operating parameters are listed in Table 1.

TABLE 1

Operating Modes and Parameters

| Ex. | Continuous Beam | | | | | Pulsed Beam | Difference/Similarity between Continuous and Pulsed Beams |
|---|---|---|---|---|---|---|---|
| | X-ray tube Current | Scan Time | Total Dose | Frame Rate | Projection Number | | |
| 1 | 30 mA | 16.6 sec at 4 rpm | 498 mAs | 30 fps | 491 | Thorax Fast Mode: X-ray tube current: 100 mA Pulse length: 10 ms Imager frame rate: 30 fps X-ray tube duty cycle: 29.6% | Same number of projections Same counts in a projection Practically same total mAs |

TABLE 1-continued

Operating Modes and Parameters

| | | Continuous Beam | | | | | |
|---|---|---|---|---|---|---|---|
| Ex. | X-ray tube Current | Scan Time | Total Dose | Frame Rate | Projection Number | Pulsed Beam | Difference/Similarity between Continuous and Pulsed Beams |
| 2 | 30 mA | 16.6 sec at 4 rpm | 498 mAs | 49 fps | 811 | Thorax Fast Mode: X-ray tube current: 100 mA Pulse length: 10 ms Imager frame rate: 30 fps X-ray tube duty cycle: 29.6% | Higher number of projections Lower counts in a projection Practically same total mAs |
| 3 | 34 mA | 16.6 sec at 4 rpm | 595 mAs | 49 fps | 855 | Thorax with Double mA X-ray tube current: 70 mA Pulse length: 10 ms Imager frame rate: 28 fps Total Beam Time: 30.8 sec. X-ray tube duty cycle: 27.9% Total Projections: 859 Total Dose: 601 mAs | Similar number of projections Similar counts in a projection Practically same total mAs Duty cycle 100% vs. 28% |

Figure 3:
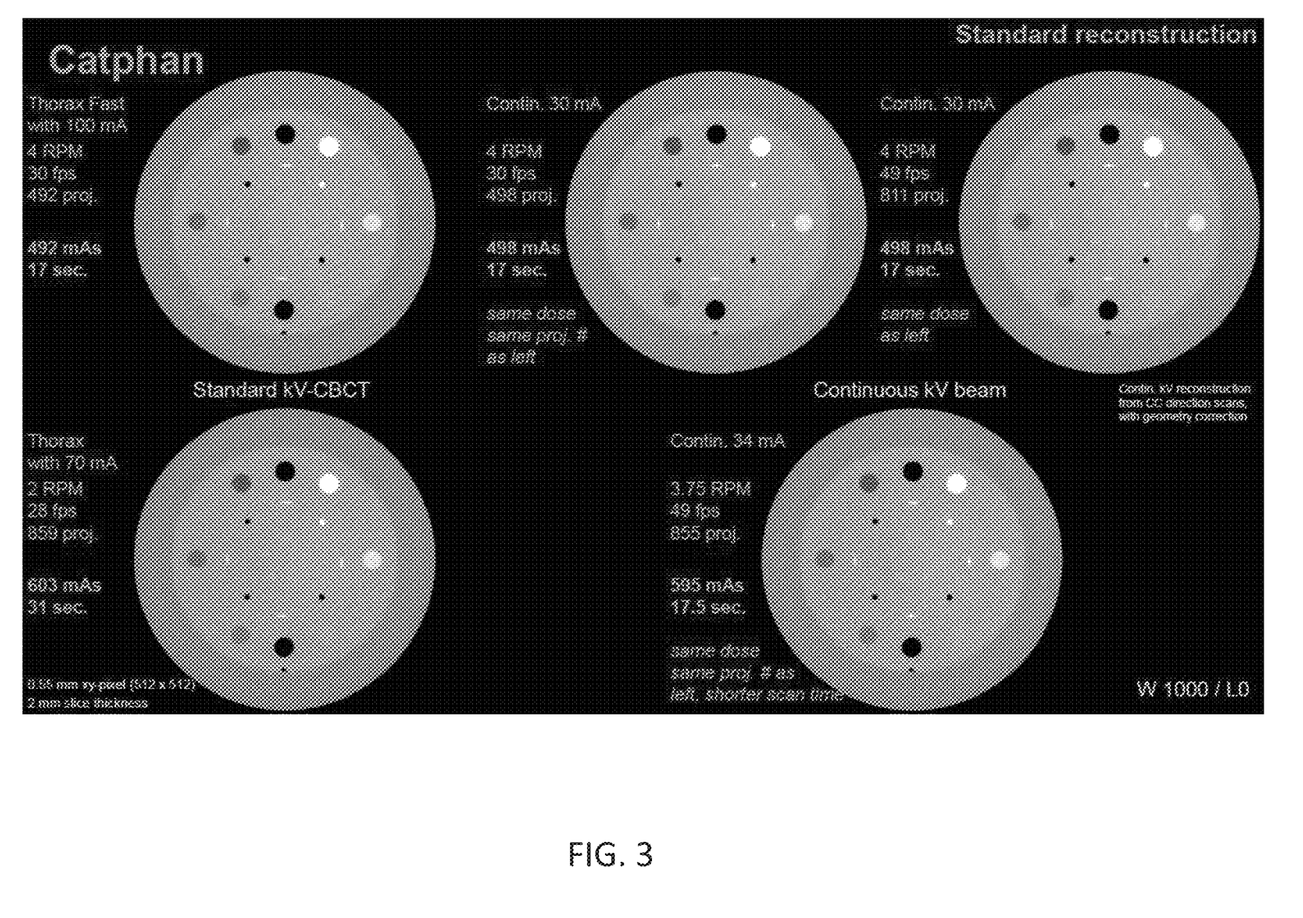
FIG. 3 shows Catphan® phantom images generated by Standard CBCT reconstruction according to embodiments of the disclosure.
Figure 4:
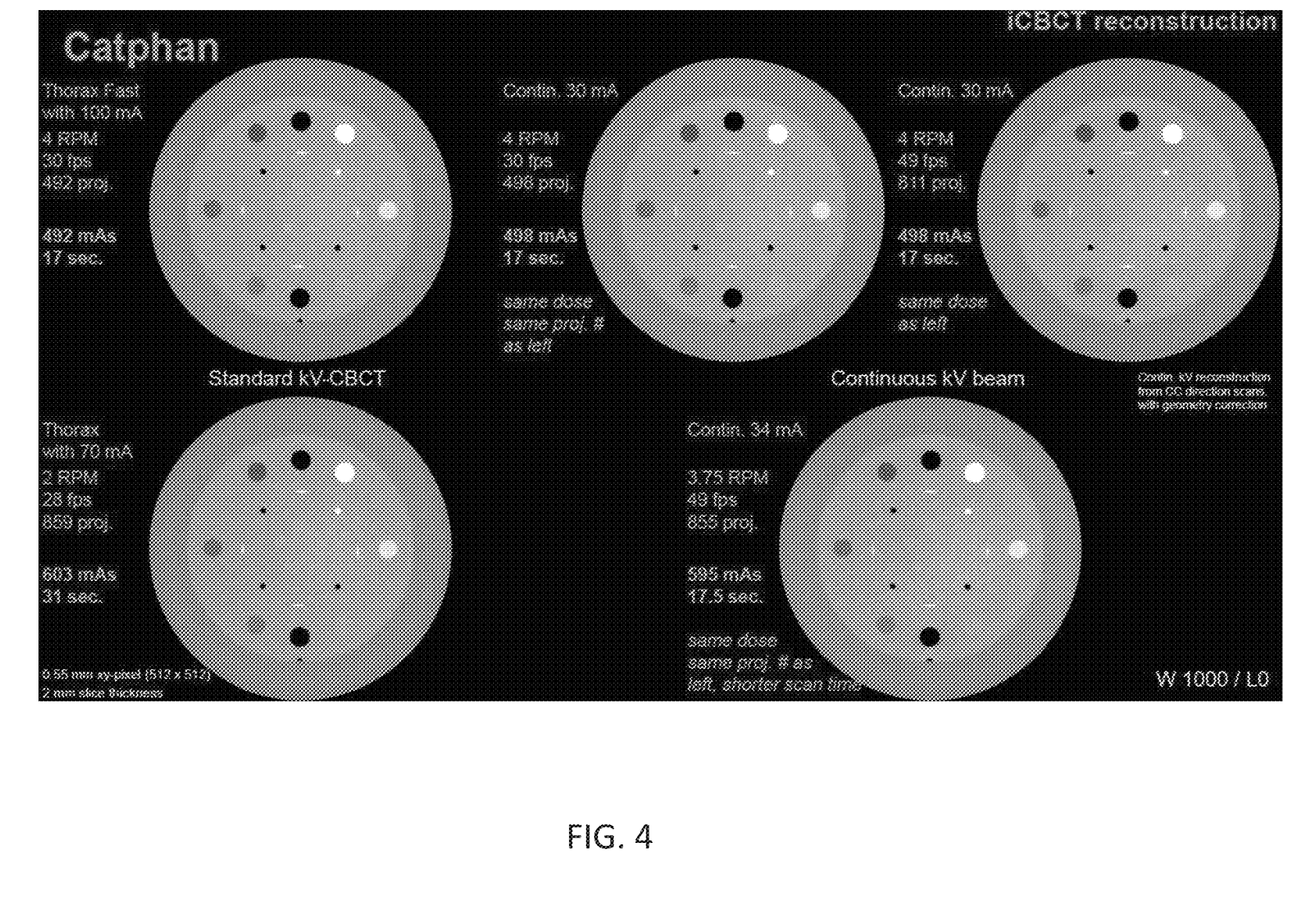
FIG. 4 shows Catphan® phantom images generated by Iterative CBCT reconstruction according to embodiments of the disclosure.
Figure 5:
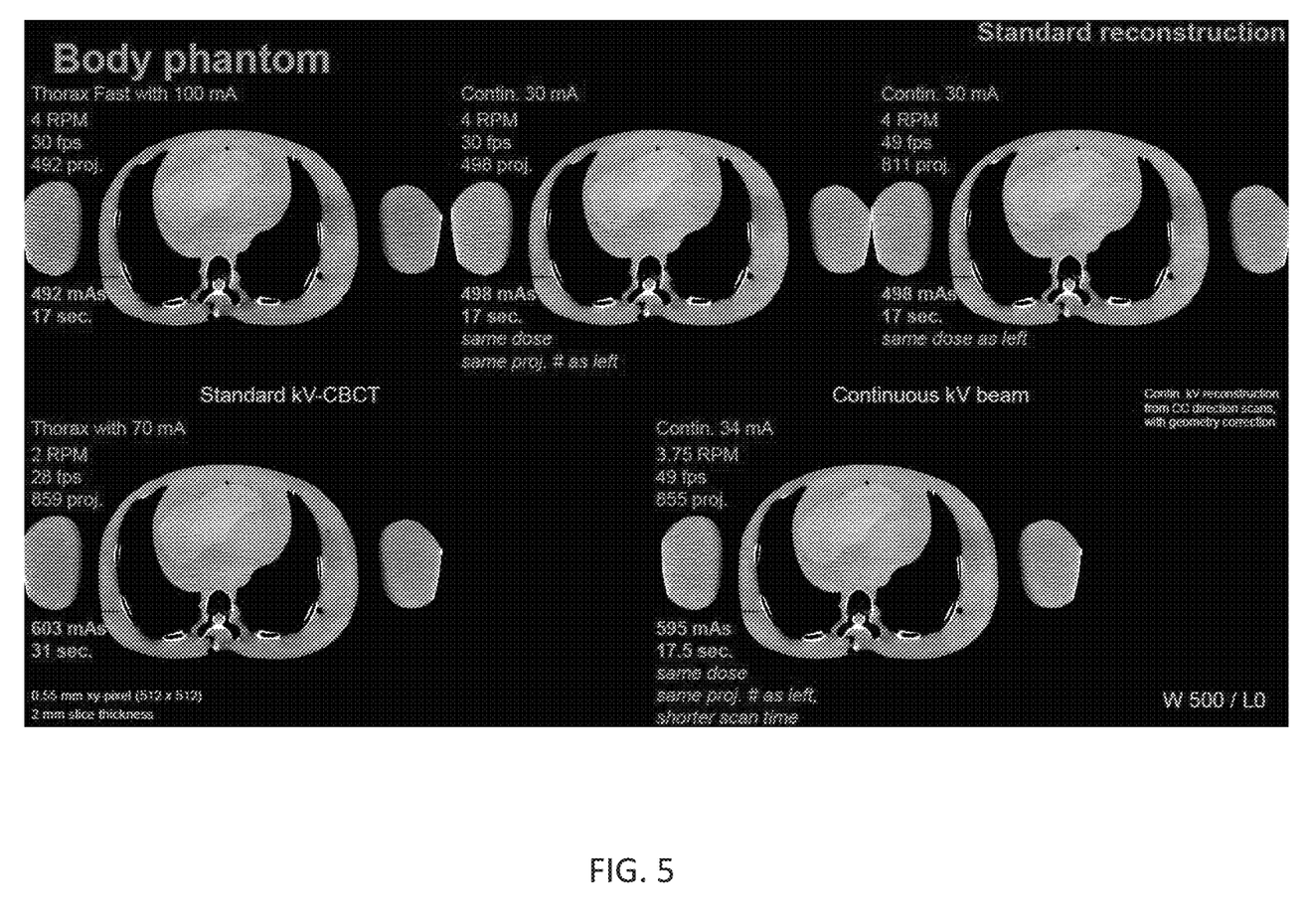
FIG. 5 shows Body phantom images generated by Standard CBCT reconstruction according to embodiments of the disclosure.

Example 1 (Ex. 1 in Table 1) was designed to test if a continuous kV beam generated results comparable to or better than that by pulsed beam acquisition using the same frame rate of a flat-panel imager. As shown in Table 1, in Example 1 the total dose delivered to the phantoms in continuous beam and pulsed beam acquisitions was practically the same, both about 498 mAs. The total number of projections acquired was also the same, both 491. The counts or values in grey level of individual pixels on a projection, was also the same. FIG. 3 shows a Catphan® phantom image on the top left generated by Standard CBCT reconstruction based on projection data acquired with a pulsed kV beam, a Catphan® phantom image on the top center generated based on projection data acquired with a continuous kV beam, under the operating parameters described in Table 1 for Ex. 1. FIG. 4 shows Catphan® phantom images generated by iterative CBCT (iCBCT) reconstruction. The Catphan® phantom images at the top left and top central on FIG. 4 show results similar to those on FIG. 3. FIG. 5 shows Body phantom images generated by Standard CBCT reconstruction. FIG. 5 on the top left shows a Body phantom image generated by Standard CBCT reconstruction based on projection data acquired with a pulsed kV beam, on the top center a Body phantom image generated based on projection data acquired with a continuous kV beam, under the operating parameters described in Table 1 for Ex. 1. The reconstructed images on FIGS. 3-5 show that the continuous kV beam acquisition generated results better than or at least as good as that generated by the pulsed beam acquisition.

Example 2 (Ex. 2 in Table 1) was designed to test if fast acquisition with a continuous kV beam generated results comparable to or better than that by pulsed beam acquisition. As shown in Table 1, in Example 2 the total dose delivered to the phantoms in continuous beam and pulsed beam acquisitions was practically same, both about 498 mAs. One difference was that with the continuous beam acquisition, the flat-panel imager was operated at a much faster readout speed, about 49 frames per second, with line time about 57.66 μs, readout time about 19.2 ms, and cycle time about 20.48 ms. As such, a higher total number of frames or projections (811) were read out with the continuous beam acquisition but the counts on each projection were lower. Nevertheless, the continuous kV beam acquisition still generated results (image quality with streaks and noise) better than or at least as good as that generated by pulsed beam acquisition, as shown in FIGS. 3-5. FIG. 3 shows a Catphan® phantom image on the top left generated by Standard CBCT reconstruction based on projection data acquired with a pulsed kV beam, a Catphan® phantom image on the top right generated based on projection data acquired with a continuous kV beam, under the operating parameters described in Table 1 for Ex. 2. FIG. 4 shows Catphan® phantom images generated by iCBCT reconstruction. The top left and top right Catphan® phantom images on FIG. 4 show results similar to those on FIG. 3. FIG. 5 shows Body phantom images generated by Standard CBCT reconstruction. FIG. 5 on the top left shows a Body phantom image generated by Standard CBCT reconstruction based on projection data acquired with a pulsed kV beam, on the top right a Body phantom image generated based on projection data acquired with a continuous kV beam, under the operating parameters described in Table 1 for Ex. 2.

Example 3 (Ex. 3 in Table 1) was designed to test if acquisition with a source operating at 100 percent duty cycle directly reduced the scan time. As shown in Table 1, in Example 3, the operating parameters were adjusted so that an approximately same total dose (595 mAs with a continuous beam versus 601 mAs with a pulsed beam) was delivered to the phantoms. An approximately same total number of projections was acquired (855 with a continuous beam versus 859 with a pulsed beam) where the counts on the projection were also similar. The total scan time was significantly reduced from about 30.8 seconds with the pulsed beam acquisition to about 17.5 seconds with the continuous beam acquisition, even though the x-ray tube current for the continuous beam acquisition was less than half of that for the pulsed beam acquisition (34 mA with a continuous beam versus 70 mA with a pulsed beam). Nevertheless, the continuous kV beam acquisition still generated results better than or at least as good as that generated by pulsed beam acquisition, as shown on FIGS. 3-5. FIG. 3 on the bottom left shows a Catphan® phantom image generated by Standard CBCT reconstruction based on projection data acquired with a pulsed kV beam, on the bottom right a Catphan® phantom image generated based on projection data acquired with a continuous beam, under the operating parameters described in Table 1 for Ex. 3. FIG. 4 are Catphan® phantom images generated by iCBCT reconstruction. The bottom left and bottom right Catphan® phantom images on FIG. 4 show results similar to those on FIG. 3. FIG. 5 shows Body phantom images generated by Standard CBCT reconstruction. FIG. 5 on the bottom left shows a Body phantom image generated by Standard CBCT reconstruction based on projection data acquired with a pulsed kV beam, on the bottom right a Body phantom image generated based on projection data acquired with a continuous kV beam, under the operating parameters described in Table 1 for Ex. 3.

Returning to FIG. 1, the radiation source 102 may be a source operable to produce photons, protons or other heavy ions, and electrons. By way of example, the source 102 may include an x-ray tube comprising a target which generates x-rays upon impingement of electrons. The x-ray tube 102 may include a collimator device to collimate the beam so that the beam exiting the x-ray tube generally in a conical or pyramidal shape. As another example, the source 102 may include a linear accelerator comprising a target which generates x-rays upon impingement of electrons, and various collimation devices for shaping and/or sizing the x-rays. As a further example, the source 102 may include a nozzle emitting protons produced by a cyclotron or synchrotron and transported to the nozzle. In general, the source 102 may produce or emit radiation suitable for imaging. For example, the source may be operated at a kilovoltage (kV) level e.g. ranging from 50 to 150 kV to produce radiation suitable for diagnostic imaging. Alternatively, the source may be operated at a megavoltage (MV) level for use with e.g. an electronic portal imaging device (EPID) to acquire images e.g. for determining patient setup or for interventional treatment or treatment plan iteration. In some embodiments, the source 102 may be a source operable at two or multiple modes, e.g. at either kV or MV energy levels to produce radiation for various applications.

In a specific embodiment, the source 102 includes an x-ray tube operable to produce x-rays. X-ray tubes are well known in the art and therefore their detailed description is omitted herein. Briefly and in general, an x-ray tube includes a source of electrons (cathode) e.g. a filament and a target e.g. a tungsten metal on a rotating plate (anode) enclosed in an evacuated envelope. A supply of current causes the filament to be heated producing electrons. A voltage applied to the evacuated envelope accelerates the electrons towards the anode striking the target to produce x-rays. The small surface area on the target producing the x-rays is referred to as the focal spot of the x-ray tube or source, the size of which may be determined by the electron beam from the cathode. The x-rays produced can be then shaped by a collimator and exit through a window in the envelope. While not shown in FIG. 1, an x-ray controller and generator set signals such as current, voltage, exposure time, and other operating parameters of the x-ray tube, and generates a voltage to be supplied to the x-ray tube. The x-ray controller and generator in turn can be controlled by the computer and control system 108.

Still with reference to FIG. 1, the area detector 104 detects the radiation transmitted through the subject 112, which is indicative of the attenuating properties or the structure of the imaging portion of the subject 112. The area detector 104 is coupled with a data acquisition system 105, which includes electronic circuitries for providing control signals, receiving and processing data signals, and outputting data to the image processing device 106. While shown as separate units in FIG. 1, the data acquisition system 105 and the area detector 104 can be integrated as a single unit controlled by the computer and control system 108.

The area detector 104 comprises a plurality of detection elements arranged in rows and columns in a two-dimensional area. In a specific embodiment, the area detector 104 includes a flat-panel imager having a flat detector surface. In an alternative embodiment, the area detector 104 has a curved detector surface. The area detector 104 may have an active detection area or size e.g. ranging from 20×20 cm$^2$ to about 45×45 cm$^2$. Various area detectors are commercially available from Varex Imaging Corporation in Salt Lake City, Utah.

In a specific embodiment of the disclosure, the area detector 104 is a flat-panel imager. The flat-panel imager may include a radiation conversion layer and a detector array. The conversion layer converts radiation such as x-ray photons to visible light. The detector array detects the visible light and converts it to electrical signals. The conversion layer may include a scintillator material which can generate visible light photons in response to x-ray radiation. As such, the detector array may include photosensitive elements which can generate electrical signals in response to the light photons generated by the scintillator material. Suitable scintillator materials include gadolinium oxysulfide ($Gd_2O_2S$:Tb), cadmium tungstate ($CdWO_4$), bismuth germinate ($Bi_4Ge_3O_{12}$ or BGO), cesium iodide (CsI), cesium iodide thallium (CsI:Tl), Thallium doped Sodium Iodide NaI(Tl) or any combination thereof. Suitable photosensitive element may include a photodiode, a photogate, or phototransistors etc. Alternatively, the conversion layer may include a photoconductor material which can convert x-ray photons to electrical charges (electron-hole pairs) directly. As such, the detector array may include electrodes at either side of the photoconductor material to collect the electrical charges generated by the photoconductor material. Suitable photoconductor materials include and are not limited to mercuric iodide ($HgI_2$), lead iodide ($PbI_2$), bismuth iodide ($BiI_3$), cadmium zinc telluride (CdZnTe), amorphous selenium (a-Se), etc.

In a specific embodiment, an example flat-panel imager 104 may include a large number e.g. hundreds of thousands or millions of detector pixels. The large number of detector pixels may be arranged in a plurality of rows and a plurality of columns forming an active detector area. In some specific embodiments, each detector pixel may include an addressable photosensitive element such as a photodiode and a switching transistor such as a thin-film transistor (TFT) or complementary metal oxide semiconductor (CMOS) transistor.

The detector array may further include a plurality of address lines and a plurality of data lines. Each of the plurality of address lines may connect a plurality of detector pixels in a row to a driver control assembly of the data acquisition system. Each of the plurality of data lines may connect a plurality of detector pixels in a column to a readout control assembly of the data acquisition system 105. The driver control assembly provides control signals for accessing a selected row of pixels. The readout control assembly provides control signals for reading out the signals from the pixels. By way of example, when it is desired to capture image signals from the detector array, a control signal from the driver control assembly drives the gates of switching elements e.g. TFTs in a selected row of pixels, and the signals stored in the selected row of pixels are readout by the readout control assembly. The signals from the selected pixels may be buffered, amplified, and converted by analog-to digital converters (ADCs) using electronics of the data acquisition system 105. The resulting digitized data signals can be then multiplexed, buffered, and transmitted to an image processing device 106 for further processing.

In operation of the detector arrays, the control signal from the driver control circuit for a row of pixels can be asserted on an address line for a predetermined period of time or line time. During assertion of the control signal, the signal from each pixel in the selected row is transmitted via column data lines to the readout control circuit where the signals on each data line are received and buffered by a corresponding charge sensitive amplifier. Hence, an entire row of image data can be captured in a line time period. With each subsequent line time period, a subsequent row of image data is captured. At the end of a "frame time" period, the entire image can be captured. In this manner, the pixels contained in the entire active detection area can be read out, row-by-row, each row in a line time period. In an alternative embodiment, the flat-panel imager may employ a split data-line where the top half of the array and the bottom half of the array are read out simultaneously. This allows the flat-panel imager to read out more rapidly, e.g., only half of the "frame time" is needed to read out the pixels. As such, the preprocessing of the projection data described above can be adapted according to the particular readout timing sequence implemented in such a readout scheme. By way of example, the flat-panel imager can operate at a speed ranging from 15 to 50 frames per second (fps), depending on the dose requirements, image resolution, and the number of projection data sets acquired.

Still with reference to FIG. 1, the image processing device may include a computer 118 and software 120 designed to process the projection data acquired and reconstruct tomographic images based on the projection data. The computer 118 may comprise a processor, memory, optionally a user interface, and a network interface. The processor may include a central processing unit (CPU) that is generally known in the art, such as an INTEL® processor or an AMD® processor, or a graphical processing unit (GPU), such as an NVIDIA® GPU, or other type of processing unit. The processor may retrieve and execute computer-executable instructions from the memory, which may cause the processor to perform any of the methods and/or steps according to the embodiments of this disclosure described above.

The memory may include any one of or a combination of volatile memory elements and nonvolatile memory elements. The memory may include a random-access memory (RAM) or other dynamic storage device for storing information and instructions to be executed by the processor, and for storing temporary variables or other intermediate information during execution of instructions by the processor. The memory may also include read-only memory (ROM) or other static storage device for storing static information and instructions for the processor. The memory may further include a data storage device such as a magnetic disk or optical disk, for storing information and instructions. The memory (e.g. a non-transitory computer-readable medium) may comprise programs (logic) for operating the computer system and for performing applications including dosimetric projection and dose calculation as described above, or other treatment planning applications. In addition, the memory may include a database storing any information that can be selected by a user, such as a radiation oncologist or radiation therapist.

The user interface device may include components with which a user interacts with the computer system, such as a keyboard, pointing device, pen, touch input device, voice input device, or the like. Output devices such as a display device, printer, speaker etc. may also be included in the computer system.

The network interface allows the computer system to communicate with other devices or systems over a communication network such as the Internet or an intranet (e.g., a local area network). The network interface may include a Wi-Fi interface, Ethernet interface, Bluetooth interface, or other wireless or wired interfaces. The network interface allows the computer system to receive and send electrical, electromagnetic or optical signals that carry data streams representing various types of information. For instance, the network interface may allow the computer system to receive data streams representing software programs for treatment planning over the communication network.

Various embodiments of a CBCT method and system are described with reference to the figures. It should be noted that some figures are not necessarily drawn to scale. The figures are only intended to facilitate the description of specific embodiments and are not intended as an exhaustive description or as a limitation on the scope of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "first" or "second" is used to distinguish one element from another in describing various similar elements and should not be construed as in any particular order unless the context clearly dictates otherwise.

Those skilled in the art will appreciate that various other modifications may be made. All these or other variations and modifications are contemplated by the inventors and within the scope of the invention.

What is claimed is:

1. A method, comprising:
acquiring a plurality of projections of data set of at least a portion of a subject using a source of radiation and an area detector movable in synchrony with the source, wherein in the acquiring of the plurality of projections of data set, the source irradiates the portion of the subject with a cone beam of radiation from a plurality of angles and the area detector reads out data indicative of a structure of the portion of the subject irradiated by the cone beam of radiation;
pre-processing at least a portion of the plurality of projections of data set; and
reconstructing a tomographic image of the portion of the subject based on the at least portion of the plurality of projections of data set pre-processed, wherein the pre-processing comprises weighting data of a given projection acquired in a given time period with data of a projection acquired after or before the given projection.

2. The method of claim 1, wherein the pre-processing comprises weighting data of the given projection with data of a projection acquired after the given projection and with data of a projection acquired before the given projection.

3. The method of claim 1, wherein in the acquiring of the plurality of projections of data set, the source is operated at a kilovoltage (kV) energy level.

4. The method of claim 1, wherein in the acquiring of the plurality of projections of data set, the source continuously irradiates the portion of the subject, and the area detector reads out data during the continuous irradiating of the portion of the subject.

5. The method of claim 3, wherein the plurality of projections of data set are acquired while the source rotates around the subject in 360 degrees or more.

6. The method of claim 1, wherein the source comprises a focal spot and produces the cone beam of radiation having a cone angle, and the area detector comprises an active detection surface spaced apart from the focal spot of the source at a distance, thereby a rotation of the source and the area detector in synchrony provides a reconstruction volume encompassing the portion of the subject, the reconstruction volume having a field of view ranging from 25 to 50 centimeters and/or a scan length ranging from 15 to 28 centimeters.

7. The method of claim 1, wherein the area detector comprises a flat-panel imager comprising a plurality of detector pixels arranged in rows and columns each having an addressable photosensitive element and a switching TFT or CMOS transistor.

8. The method of claim 6, wherein the flat-panel imager comprises an active detection area of about 40×40 cm$^2$ or larger.

9. The method of claim 1, wherein the weighting of data of the given projection comprises giving a weight to a data value of a pixel of a given row (y) based on a time lapse in reading out data of the given row (y) relative to a reference row (y0).

10. The method of claim 9, wherein the weighting of data of the given projection is carried out according to the following linear interpolation:

replace $p_i(\ldots, y)$ by:

$$w*p_i(\ldots,y)+(1-w)*p_{i+1}(\ldots,y), \text{where}$$

$p_i(\ldots,y)$ represents a data value of a pixel at row y of a given projection i acquired by the area detector comprising h rows of pixels and y<h/2, $p_{i+1}(\ldots,y)$ represents a data value of the pixel at row y of projection i+1, w represents a weighting factor, and w=1−(h/2−y)*(line Time/cycleTime), lineTime represents a time period elapsing between readout of successive rows, and cycleTime represents a time period elapsing between readout of successive projections, or replace $p_i(\ldots,y)$ by:

$$w*p_i(\ldots,y)+(1-w)*p_{i-1}(\ldots,y), \text{where}$$

$p_i(\ldots,y)$ represents a data value of a pixel at row y of a given projection i acquired by the area detector comprising h rows of pixels and y>h/2, $p_{i-1}(\ldots,y)$ represents a data value of the pixel at row y of projection i−1, w represents a weighting factor, and w=1−(y−h/2)*(line Time/cycleTime)

lineTime represents a time period elapsing between readout of successive rows, and cycleTime represents a time period elapsing between readout of successive projections.

11. A method, comprising:
acquiring a plurality of projections of data set of at least a portion of a subject using a source of radiation and an area detector movable in synchrony with the source, wherein in the acquiring of the plurality of projections of data set, the source continuously irradiates the portion of the subject with a cone beam of radiation from a plurality of angles and the area detector reads out data during the continuous irradiating of the portion of the subject with the cone beam of radiation, the area detector comprising a plurality of detector pixels arranged in rows and columns:
pre-processing at least a portion of the plurality of projections of data set; and
reconstructing a tomographic image of the portion of the subject based on the at least portion of the plurality of projections of data set pre-processed, wherein the pre-processing comprises weighting data of a given projection acquired in a given time period, comprising:
determining readout time of each of the rows of the given projection, setting a timestamp for the given projection using the readout time of a reference row, and weighting data of a row having readout time earlier than the timestamp using data of a projection acquired after the given projection.

12. The method of claim 11, further comprising weighting data of a row having readout time later than the timestamp using data of a projection acquired before the given projection.

13. The method of claim 12, wherein the reference row is associated with a central row of the area detector.

14. The method of claim 12, wherein the weighting of data of the given projection comprises giving a weight to a data value of a pixel of a given row (y) based on a time lapse in reading out data of the given row (y) relative to the reference row (y0) according a linear interpolation.

15. The method of claim 14, wherein the weighting of data of the given projection is carried out according to the following linear interpolation:

replace $p_i(\ldots,y)$ by:

$$w*p_i(\ldots,y)+(1-w)*p_{i+1}(\ldots,y), \text{where}$$

$p_i(\ldots,y)$ represents a data value of a pixel at row y of a given projection i acquired by the area detector comprising h rows of pixels and y<h/2, $p_{i+1}(\ldots,y)$ represents a data value of the pixel at row y of projection i+1, w represents a weighting factor, and w=1−(h/2−y)*(line Time/cycleTime), lineTime represents a time period elapsing between readout of successive rows, and cycle Time represents a time period elapsing between readout of successive projections, or replace $p_i(\ldots,y)$ by:

$$w*p_i(\ldots,y)+(1-w)*p_{i-1}(\ldots,y), \text{where}$$

$p_i(\ldots,y)$ represents a data value of a pixel at row y of a given projection i acquired by the area detector comprising h rows of pixels and y>h/2, $p_{i-1}(\ldots,y)$ represents a data value of the pixel at row y of projection i−1, w represents a weighting factor, and w=1−(y−h/2)*(line Time/cycleTime)

lineTime represents a time period elapsing between readout of successive rows, and cycle Time represents a time period elapsing between readout of successive projections.

16. The method of claim 11, wherein the plurality of projections of data set are acquired while the source rotates around the subject in 360 degrees or more.

17. The method of claim 11, wherein the source comprises a focal spot and produces the cone beam of radiation having a cone angle, and the area detector comprises an active detection surface spaced apart from the focal spot of the source at a distance, thereby a rotation of the source and the area detector in synchrony provides a reconstruction volume encompassing the portion of the subject, the reconstruction volume having a field of view ranging from 25 to 50 centimeters and/or a scan length ranging from 15 to 28 centimeters.

18. The method of claim 11, wherein the area detector comprises a flat-panel imager comprises an active detection area of about 40×40 cm² or larger.

19. The method of claim 11, wherein in the acquiring of the plurality of projections of data set, the source is operated at a kilovoltage (kV) level.

* * * * *